(12) United States Patent
Poteet et al.

(10) Patent No.: US 7,106,826 B2
(45) Date of Patent: Sep. 12, 2006

(54) SYSTEM AND METHOD FOR ADAPTING A SOFTWARE CONTROL IN AN OPERATING ENVIRONMENT

(75) Inventors: Wade M. Poteet, Tucson, AZ (US); Harold K. Cauthen, Sonoita, AZ (US); Timothy D. Shriver, Tuscon, AZ (US)

(73) Assignee: CDEX, Inc., Rockville, MD (US)

( * ) Notice: Subject to any disclaimer, the term of this patent is extended or adjusted under 35 U.S.C. 154(b) by 40 days.

(21) Appl. No.: 10/268,678

(22) Filed: Oct. 11, 2002

(65) Prior Publication Data

US 2003/0128804 A1    Jul. 10, 2003

Related U.S. Application Data

(60) Provisional application No. 60/344,787, filed on Jan. 7, 2002.

(51) Int. Cl.
*G01N 23/223* (2006.01)

(52) U.S. Cl. .......................................... 378/45; 378/57

(58) Field of Classification Search ................. 378/44, 378/45, 48, 49, 50, 57; 250/253, 269.1, 358.1, 250/370.09
See application file for complete search history.

(56) References Cited

U.S. PATENT DOCUMENTS

| | | | | |
|---|---|---|---|---|
| 5,937,026 A | * | 8/1999 | Satoh | 378/44 |
| 6,178,227 B1 | | 1/2001 | Sato | 378/117 |
| 6,266,390 B1 | * | 7/2001 | Sommer et al. | 378/45 |
| 6,459,767 B1 | * | 10/2002 | Boyer | 378/121 |
| 6,501,825 B1 | | 12/2002 | Kaiser et al. | 378/45 |
| 6,519,315 B1 | | 2/2003 | Sommer, Jr. et al. | 378/45 |

* cited by examiner

*Primary Examiner*—Courtney Thomas
(74) *Attorney, Agent, or Firm*—Hogan & Hartson LLP (57) ABSTRACT

A system and method for detecting a substance using x-ray fluorescence is disclosed. The detected substances may be explosives or controlled substances that have a specific chemical fluorescent signature. An energy source transmits an x-ray beam at a target. The target may be in a container or under a surface. The beam interacts with the target to produce fluorescent energy. An x-ray detector is at an angle relative to the energy source and gathers the fluorescent energy. The angle differs according to the physical configuration of the system. A portable embodiment will have a different angle than a stationary embodiment. A cooling mechanism cools the x-ray detector. The fluorescent energy is analyzed and processed by a multichannel analyzer and a computer. The computer determines whether the fluorescent energy from the target matches known fluorescent energies of specific substances. If the substance is detected, appropriate indications are made to prevent damage or acceptance of the substance.

21 Claims, 5 Drawing Sheets

SYSTEM AND METHOD FOR ADAPTING A SOFTWARE CONTROL IN AN OPERATING ENVIRONMENT

CROSS REFERENCE TO RELATED APPLICATIONS

This application claim benefit of U.S. Provisional Patent Application No. 60/344,787 entitled "Method and Apparatus for Substance Detection, Inspection, and Classification Using X-ray Fluorescence," filed Jan. 7, 2002, which is hereby incorporated by reference.

BACKGROUND OF THE INVENTION

1. Field of the Invention

The present invention relates to substance and material identifying, including detection, inspection, and classification. More particularly, the present invention relates to a method and system operating in the x-ray portion of the electromagnetic spectrum to identify specific elements and unique mixtures of elements that are components in controlled substances.

2. Discussion of the Related Art

Detection of explosives and controlled substances is increasing in importance. Whether at the airport, a building, or in military applications, quick and confident detection is needed for safety and convenience. Detection techniques are preferable to random searches that require one to make their selves and bags available for visual searches. Plus, detection techniques may be employed for a higher confidence level that everyone or everything has been subjected. Current detection techniques may include neutron activation analysis, x-ray absorption and scattering, resonance fluorescence directly on nuclei in the substance, quadrupole resonance with the nucleus of atoms, and various chemical sensors.

Neutron activation may require a large energy source, such as an accelerator, that consumer high power to be capable of measuring the ratios of atomic constituents directly, such as hydrogen, oxygen, nitrogen, and carbon. X-ray absorption and scattering may require complex predictive software, which may result in a high false alarm rate. Resonance fluorescence may require a large, complex energy source for operation. Quadrupole resonance techniques may suffer from a short range of reliable detection. Chemical sensors may have a slow response and a short range, and may not operate reliably under certain environmental conditions, such as high humidity.

SUMMARY OF THE INVENTION

Accordingly, the present invention is directed to a method and system for identifying substances using x-ray fluorescence. Substances may include explosives or controlled substances. These substances may have certain chemical properties that make them identifiable. The disclosed embodiments may include a low power system having increased reliability that is capable of operating at large, safe standoff distances from suspected substances without a large energy source, predictive software, or high power consumption. Unattended operation may be possible, and a decreased response time provides identification of suspect substances in a quicker and more reliable manner.

The disclosed embodiments may be advantageous in numerous settings to detect substances using a thorough and non-intrusive manner. The disclosed embodiments may be incorporated into processes, systems, and apparatuses desiring remote, non-invasive sensing of multiple elements in complex mixtures. For example, the disclosed embodiments may be utilized for high explosive monitoring and detection, land mine explosive constituent detection, and controlled substance detection in secured buildings, areas, and the like. Further, the disclosed embodiments may be utilized to control internal and external perimeter pollution and contaminant at industrial plant sites, to monitor effluent from nuclear plants and test sites, to monitor and control waste dump sites, to monitor nuclear, biological, and chemical weapons by-products and hazardous emissions, and the like. By using x-rays, the disclosed embodiments may enhance the detection and removal of buried land mines, unexploded ordinance, and other explosive devices.

Additional features and advantages of the invention will be set forth in the description that follows, and in part will be apparent from the description, or may be learned by practice of the invention. The objectives and other advantages of the invention will be realized and attained by the structure particularly pointed out in the written description and claims hereof as well as the appended drawings.

According to the disclosed embodiments, a system for detecting a substance is disclosed. The system includes an energy source to transmit an x-ray beam at a target to produce fluorescent energy. The system includes an x-ray detector to detect the fluorescent energy from the target. The x-ray detector is at an angle relative to the energy source. The system includes a multichannel analyzer to receive the fluorescent energy from the x-ray detector. The system includes a computer coupled to the multichannel analyzer to determine whether the fluorescent energy corresponds to the substance.

According to the disclosed embodiments, a portable system for detecting a substance under a surface is disclosed. The portable system includes a detection module and a support module. The portable system includes an energy source within the detection module to transmit an x-ray beam at a surface location. The energy source is mounted on an equipment support. The portable system also includes an x-ray detector within the detection module to detect fluorescent energy from a vapor plume corresponding to the surface location. The x-ray detector is at an angle relative to the energy source and mounted on the equipment support. The portable system also includes a portable multichannel analyzer within the support module to receive the fluorescent energy. The portable system also includes a computer within the support module coupled to the portable multichannel analyzer to determine whether the fluorescent energy corresponds to the substance. The portable system also includes a battery within the support module to supply power to the detection module and the support module.

According to the disclosed embodiments, a method for detecting a substance is disclosed. The method includes directing an x-ray beam at a target from an energy source. The method also includes interacting the target with the beam to produce fluorescent energy. The method also includes detecting the fluorescent energy from an x-ray at an angle from the energy source. The method also includes analyzing the fluorescent energy to determine whether the fluorescent energy corresponds to the substance.

According to the disclosed embodiments, a method for detecting a substance is disclosed. The method includes providing power to an energy source to transmit an x-ray beam. The method also includes producing fluorescent energy from an item in response to the x-ray beam. The method also includes detecting the fluorescent energy over an integration period at an x-ray detector. The method also includes processing the fluorescent energy. The method also includes determining whether the item is the substance according to the fluorescent energy.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiment of the present invention, examples of which are illustrated in the accompanying drawings.

X-ray fluorescence has been used to characterize elements and compounds. Both concentration and species may be deduced from de-convolving the spectra. X-ray beams from the excitation source may be directed toward a target area using, for example, capillary optics or collimators to define or concentrate the photons. Photoelectric interactions with the target material produce wavelength-shifted emissions that may be at longer wavelengths, or lower energies, than the absorbed excitation x-rays. The incident x-rays of the appropriate energies may be absorbed by the first or second shell orbital electrons surrounding the atom that causes the electrons to break free of the nuclear attraction.

The electrons may be in unique energy environments that are different for each element. Electrons from higher orbital energy states may drop down and fill the vacancies left by the ejected electrons. Discreet energies lost in this process of dropping down may result in emission of characteristic x-rays that are unique in energies for each element. The spectra of return photon flux for these unique energies are detected with a sensor, and analyzed with a multichannel analyzer for energy discrimination. Each different material in the target area produces a unique spectrum that is stored for comparison during the identification process that takes place when viewing an unknown sample. The excitation source characteristics are important to maximize the sensitivity of the process. The source flux preferably is variable to optimize the incident flux for photoelectric absorption without exciting unwanted constituents. The energy continuum may be slightly above the highest characteristic x-ray to be excited in order to optimize the absorption cross-section.

The disclosed embodiments may use preferred values for the maximum transmission of long-wavelength x-rays in air at various pressures and path lengths. The disclosed embodiments use theoretical path lengths of 3 meters at MSL that may be supported with a mean transmission of about 30%. The scattering from the materials in the x-ray path, such as air and dust, however, may limit the practical operating distance to about 1 to about 2 meters.

The disclosed embodiments also may have to account for clutter. Clutter may be defined as any unwanted x-ray flux reaching the detector that does not contribute directly to the identification of a material of interest. For example, in the case of buried landmine detection, clutter may arise from exciting certain metals in the target area, exciting materials close to the detector/emitter region, return flux from plant parts, exciting discarded cans or shell casings, scattering from the air or dust in the x-ray path. Because the disclosed embodiments are capable of discriminating between the various constituents of the return signal, clutter removal may be performed in software using appropriate algorithms.

The disclosed embodiments also may be subjected to theoretical sensitivity limits that depend on several factors. The factors include source energy available at the target of interest, cross-section for photoelectric absorption, path length, detector collecting area, detector energy resolution, detector geometrical characteristics, integration time, detector noise limit, and the like. For example, a preferred embodiment may use a microfocus tungsten target continuous output source. The output available at full power is 101 R/min, about 19% may be collected by an appropriate optic and directed at the target area. The expanding beam from the source may be concentrated using a collimating optic to provide an illumination spot of about 200 mm at about 1 meter standoff from the target. Cross-section for photoelectric absorption may be optimized for each material type in the sampling program by rapid computer controlled adjustment of source accelerating potential and flux. A number of quick exposures may be taken for the excitation energies of interest from a database of known materials that are likely to be in the target region.

The preferred implementation detector collecting area is in the range of about 200 $mm^2$ to about 1018 $mm^2$ with no optic. This area allows for a reliable detection range for explosives of about one to about two meters depending on the material species and the concentration. The detector may be a commercial germanium detector that is modified for long wavelength, or low energy, application, and may have the following preferred values:

Energy resolution (eV)–about 190 to about 300
Collecting area ($mm^2$)–about 200 to about 1018
Noise @ gain=100 (counts rms) of +/−0.7

Integration times of about 5 to about 45 seconds per species at a maximum of about two meters standoff may be used to provide the system computer with sufficient data for accurate identifications. A lead collimator or optic attached near the front of the entrance window may provide a reliable geometrical beam for the detector. The beam may be limited to about 200 $mm^2$ at a standoff of about one meter.

Figure 1:
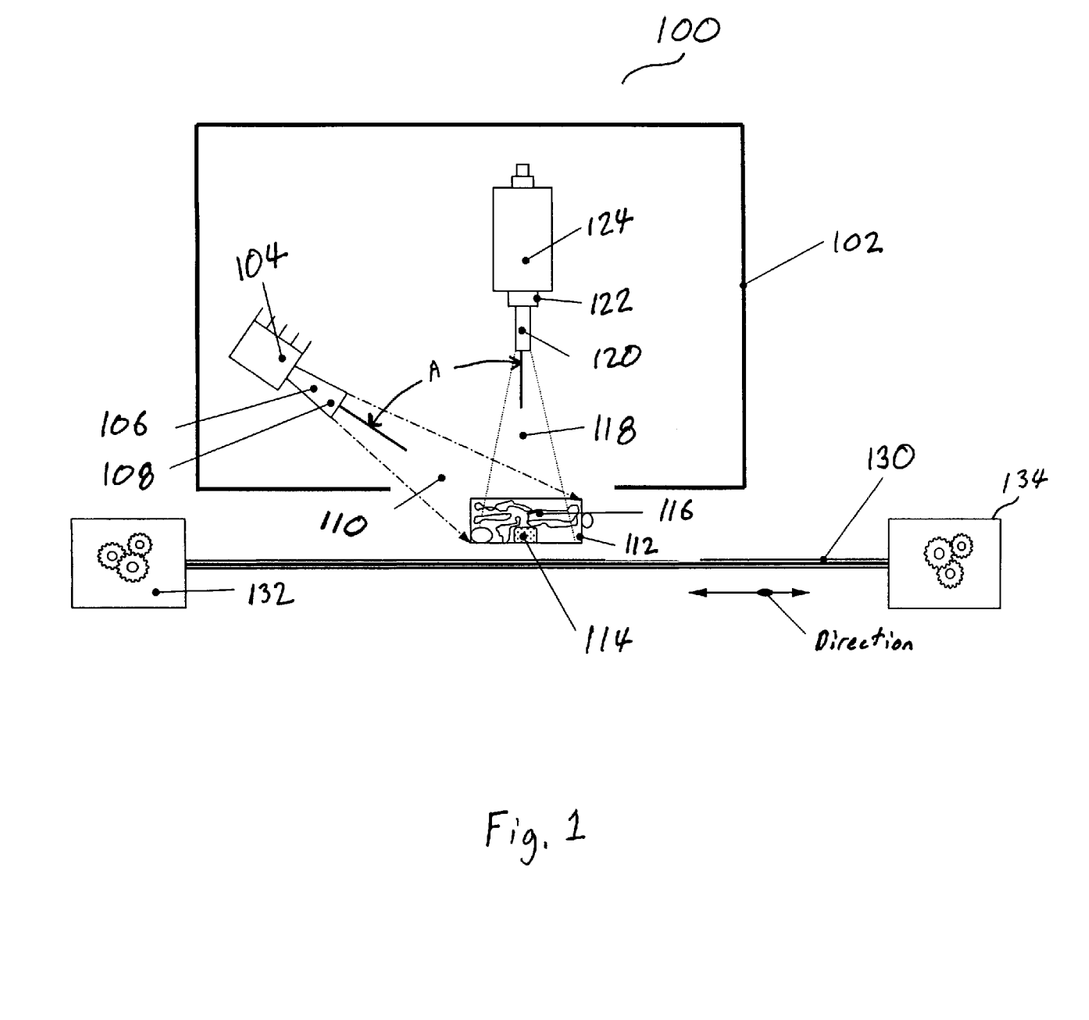
FIG. 1 illustrates an x-ray fluorescence detection system according to the disclosed embodiments.

Referring to FIG. 1, an x-ray fluorescence detection system 100 is depicted according to the disclosed embodiments. Detection system 100 may be configured for detection of controlled and other dangerous substances located in containers or suitcases. Detection system 100 includes an x-ray shielded enclosure 102 to minimize exposure to radiation by personnel. Detection system 100 also includes an energy source 104 fitted with a collimator 106 and optic 108. In an alternative embodiment, optic 108 may be removed. An angle A may exist between the central axes of energy source 104 and x-ray detector 122. Preferably, angle A is about 45 degrees to about 65 degrees. More preferably, angle A is about 57 degrees.

X-rays are directed from source 104 through collimator 106 and optic 108 along source beam 110 towards a container 112. Container 112 may be luggage, suitcase, box, briefcase, bag, or any container suspected of containing controlled material 114. Intervening material 116 may be present in container 112 as well. Controlled material 114 may be explosives, chemicals, controlled substances, and the like. Intervening material 116 may be any material or items that are not being searched for, such as clothes, papers, and the like.

Intervening materials 116 and controlled material 114 are excited by the appropriate energy from source 104 via source beam 110 to produce fluorescent energy components. Detector beam 118 is comprised of the produced energy components. Detector collimator 120 captures detector beam 118 to deliver to x-ray detector 122. Cooling mechanism 124 cools x-ray detector 122 its preferred operating temperature. Cooling mechanism 124 may be passive, using liquid nitrogen, or active, using a mechanical refrigerator assembly.

During an integration period, detection system 100 gathers x-rays for a period of time. Container 112 may be stationary for the integration period. Preferably, the integration period is from about 5 seconds to about 45 seconds. Multiple detectors 122 may be used to increase area coverage and to shorten the integration period. Container 112 is maneuvered into source beam 110 and detector beam 118 by conveyor 130. Conveyor 130 may move in either direction and may be controlled by conveyor controllers 132 and 134. The disclosed embodiments enable the x-rays to penetrate container 112 and to excite fluorescence directly in controlled material 114 without effluent or plume.

The preferred components for energy, or x-ray, source 104 are disclosed below. The excitation source may be a small filamentary solid target x-ray tube integrated with a high voltage power supply into a single unit, or source 104. Air cooling and low operating power are features of source 104. The target is tungsten and may produce a source spot size of about 0.25 mm×about 0.45 mm. A thin about 0.13 mm Beryllium window is located near the source target. Extensive shielding around the exit window and nearby structure may be sufficient to ensure that leakage is less than about 0.5 mR/hour, measured about 1 inch away from source 104, except directly in front of the window. Illumination angle may be 35 degrees. Thus, collimator 106 and optic 108 may be close to the exit window to capture as much energy as possible, and to re-direct the energy to container 112 and controlled material 114.

The preferred components for x-ray detector 122 are disclosed below. Detector 122 may be a high purity germanium crystal or any x-ray detector whose length is selected for the energy range used for the explosive constituent measurement. Energy resolution and response time may be enhanced through an ultra-thin contact arrangement. Detector 122 may be cooled to 77 degrees Kelvin using a small pour-filled liquid nitrogen dewar or a mechanical refrigerator in cooling mechanism 124. Alternatively, any known component used for cooling may be utilized by cooling mechanism 124. Energy resolution is disclosed in greater detail below. A portable self-contained liquid nitrogen system may provide sufficient coolant for daily fills during field operations.

Figure 2:
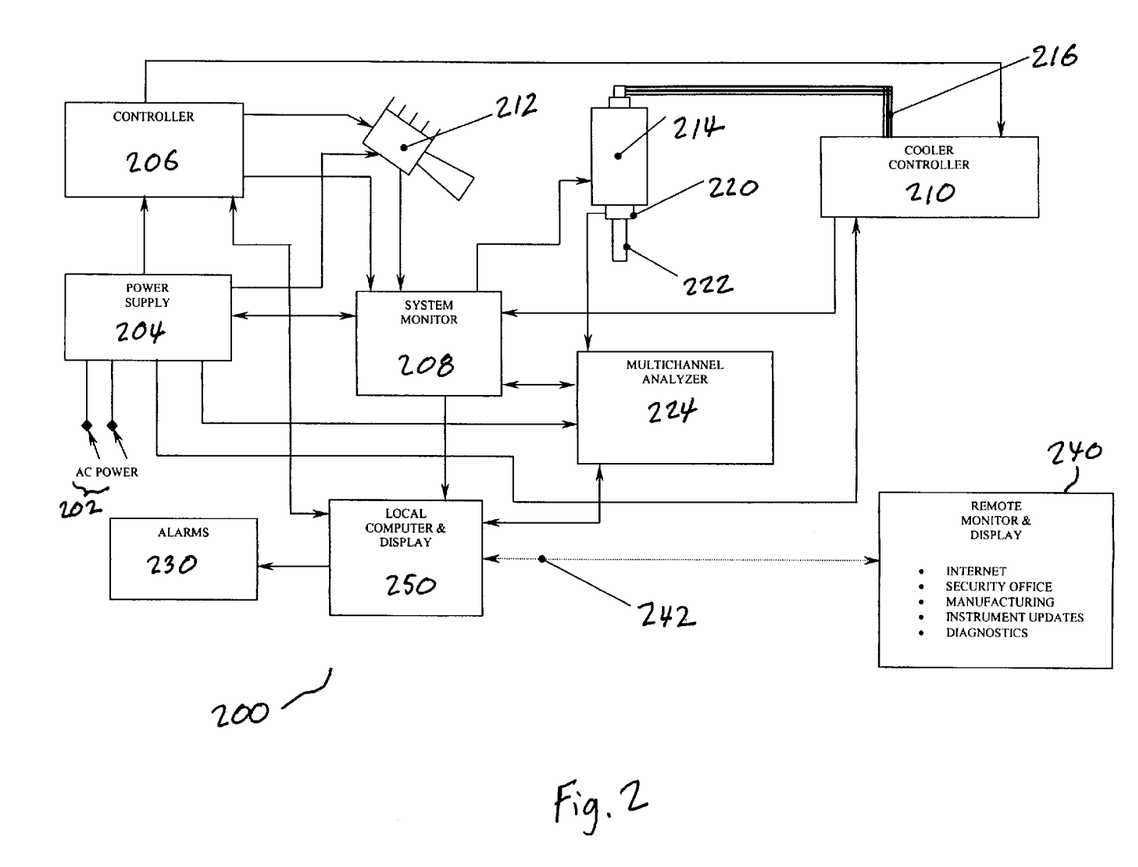
FIG. 2 illustrates a block diagram of an x-ray fluorescence detection system according to the disclosed embodiments.

X-ray detector 122 may pass through an annealing process, as disclosed below. An annealing process enhances the low energy performance of detector 122 at the expense of higher energies. Low energy may be defined as about 2 keV to about 10 keV, while high energy may be defined as about 15 keV to about 200 keV. The annealing process may be implemented on a commercial pure Germanium detector crystal. The annealing process may be used without dismounting detector 122 from its commercially received package. The electronic components, however, may be removed for the annealing process. The annealing process may execute, as follows:

1. Set max temperature to about 365 degrees Fahrenheit
2. Set nom temperature to about 312 degrees Fahrenheit
3. Introduce nitrogen gas flow through the oven, wherein the nitrogen gas may be an effluent from a liquid nitrogen container
4. Place detector in an oven and anneal for about 24 hours
5. Cycle temperature down at a rate of about 20 degrees Fahrenheit per hour until room temperature is achieved while maintaining flow of nitrogen gas
6. Cool detector to 77 degrees Kelvin
7. Repeat steps 1 through 6, preferably at least once
8. Replace crystal detector electronics, re-evacuate crystal detector housing
9. Measure detector risetime after bias stabilization to verify $\leq$ about 0.5 microseconds
10. Repeat anneal if risetime has not been achieved FIG. 2 depicts a block diagram of an x-ray fluorescence detection system 200 according to the disclosed embodiments. Detection system 200 may correlate to detection 100 depicted in FIG. 1. Power is supplied to detection system 200 through external power supply 202, or any local power source. Power from external power supply 202 is used by power supply 204 to furnish appropriate voltages and currents to system controller 206 and system monitoring subsystem 208. Additional power may be routed to cooler controller 210 through controller 206.

X-ray source 212 receives power and control from controller 206. The status of x-ray source 212 is reported to system monitor 208 for formatting and routing to local computer 250. Cooler controller 210 provides coolant flow to cooling mechanism 214 via coolant lines 216. Cooler controller 210 reports its condition and status to system monitor 208. Power for x-ray detector 220 is supplied through system monitor 208. Data from x-ray detector 220 is routed through multichannel analyzer 224 to local computer 250 for display, processing, and the like. Local computer may be any device or component having a processor coupled to a memory, wherein the memory stores instructions to execute on the processor. Local alarms 230 indicate detection of certain materials. Data may be transmitted simultaneously through transmission link 242 to a remote monitor and display 240. Transmission link 242 may include, but is not limited to, the internet, hard wiring, optical links, radio frequency links, virtual networks, local area networks, wide area networks, coaxial cables, and the like. Remote monitor and display 240 may be located in a security office or a manufacturer's facility in order to provide diagnostics and updates to detection system 200.

Figure 3:
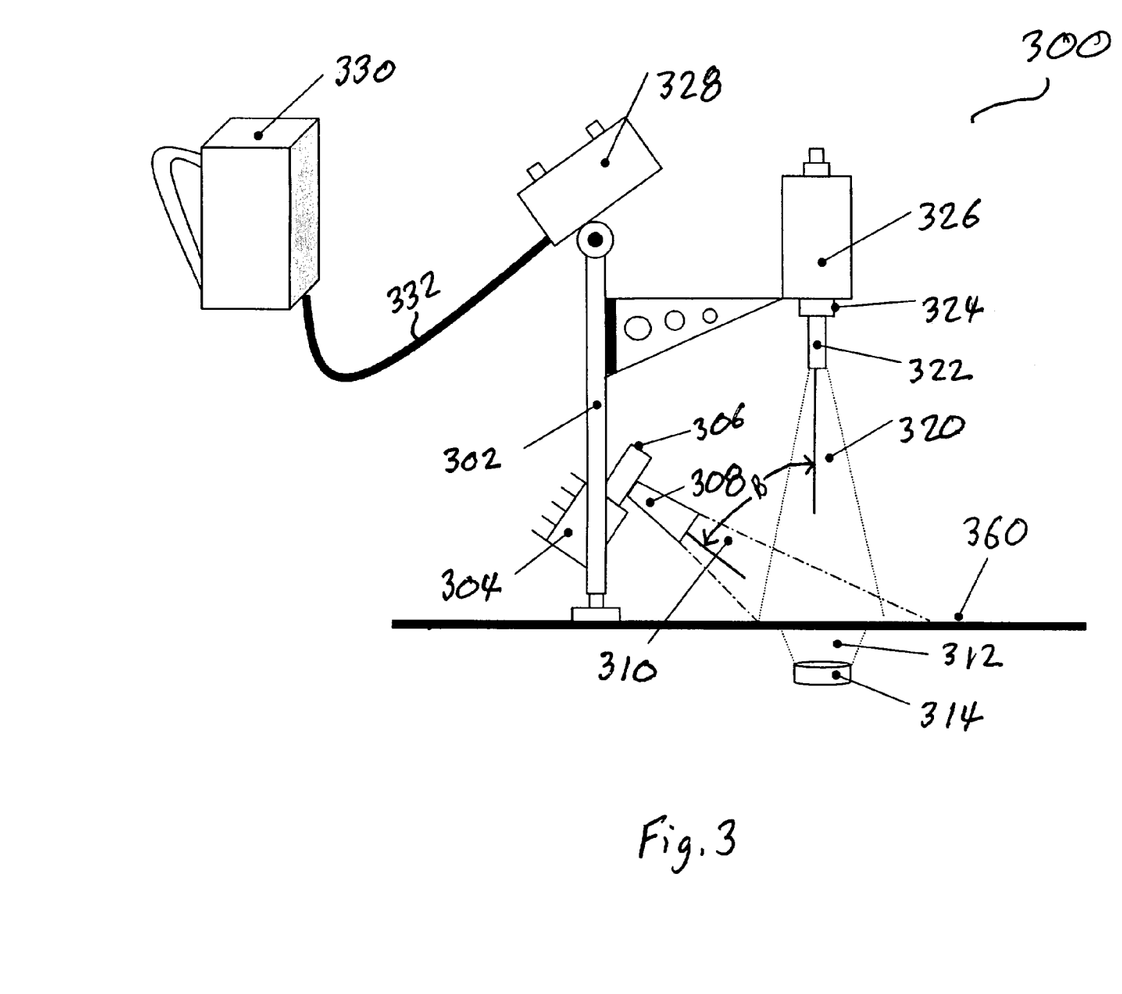
FIG. 3 illustrates an x-ray fluorescence detection system for detection of concealed substances and explosives buried in the ground or hidden beneath a surface in accordance with disclosed embodiments.

FIG. 3 depicts an x-ray fluorescence detection system 300 for detection of concealed substances and explosives buried in the ground or hidden beneath a surface 360 in accordance with disclosed embodiments. Detection system 300 preferably is mounted on equipment support 302 that allows portability to the site of suspected substances, such as explosives. Detection system 300 contains an energy source 304 fitted a source collimator 306 and optic 308. Alternatively, detection system 300 may not include optic 308. X-rays are directed from energy source 304 through collimator 306 and through optic 308 along source, or x-ray, beam 310. Source beam 310 is directed toward a vapor plume 312 that arises from a buried or concealed substance 314 underneath surface 360.

Materials within vapor plume 312, at or near surface 360, including concealed substance 314, are excited by the appropriate energy from energy source 304 to produce fluorescent energy components into detector beam 320. Detector beam 320 passes through detector collimator 322 to x-ray detector 324. Cooling mechanism 326 cools X-ray detector 324 to its appropriate operating temperature. Cooling mechanism 326 may be passive using liquid nitrogen, or active using a mechanical refrigerator. Detector 324 gathers x-rays for a period of time known as an integration period. Components of detection system 300 should remain stationary for the integration period. The integration period may be about 5 to about 45 seconds. Multiple detectors 324 may be used to increase are coverage and shorten the integration period.

Readout, or control, box 328 may initiate the detection process and display the result of the detection process, for example, by activating appropriate lights or indicators on a display panel. Control, power, and data analysis may be provided by components in backpack 330. Backpack 330 may be toted, carried, or worn on an operator's body. Preferably, the components of backpack 330 have a weight that allows it to be carried comfortably by the operator. Detection system 300 also should be portable, and preferably is contained on one device used to detect concealed substance 314.

Thus, detection system 300 may be carried on a person, with source 304, detector 324, collimator 322, and cooling mechanism 326 coupled to backpack 330. Detection system 300 may be used as minesweeper, or mine detector. Alternatively, detection system 300 may be used by personnel within a building to detect controlled substance, explosives, and the like, underneath floors, or other surfaces.

Figure 4:
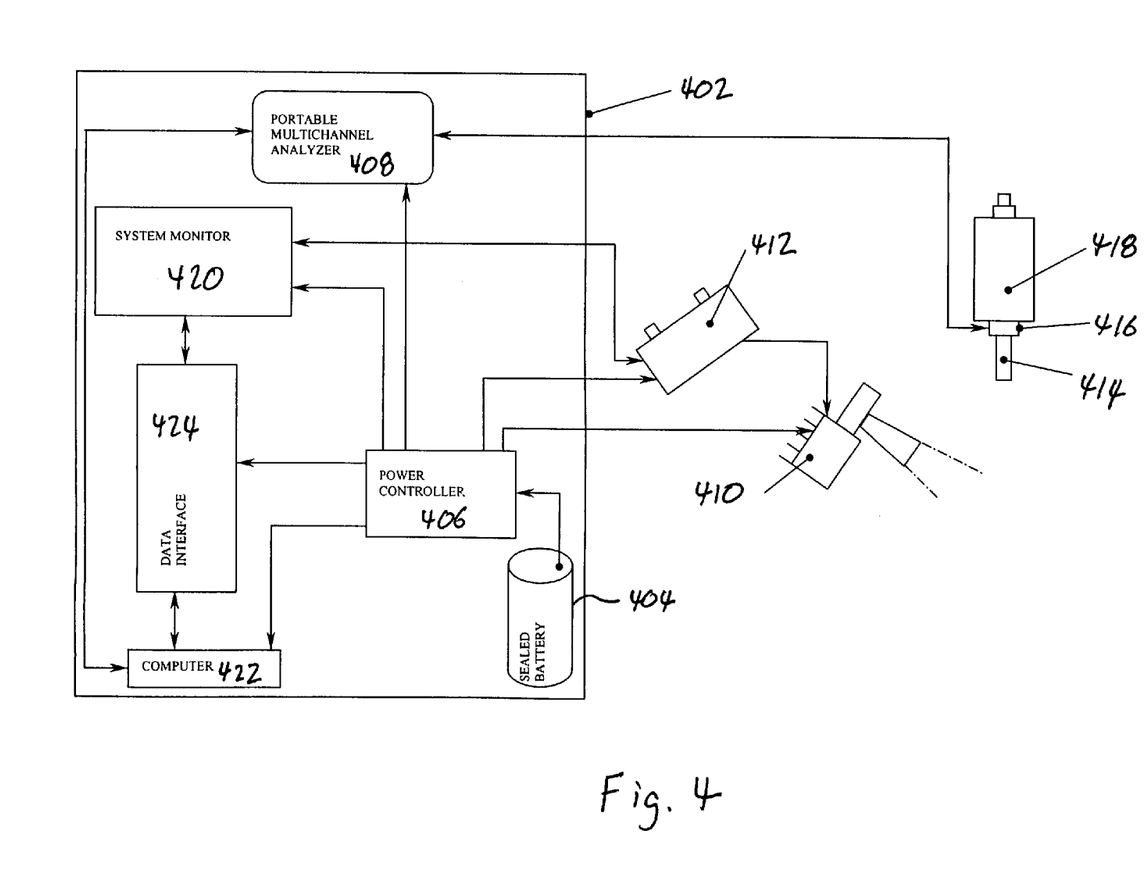
FIG. 4 illustrates a block diagram of a portable x-ray fluorescence detection system according to the disclosed embodiments.

FIG. 4 depicts a block diagram of a portable x-ray fluorescence detection system 400 according to the disclosed embodiments. Detection system 400 correlates to detection system 300 disclosed above. Detection system 400 includes backpack 402. Backpack 402 may contain various components of detection system 400, as disclosed below. Power may be supplied to detection system 400 from sealed battery 404, or any other local power source. Power controller 406 regulates and distributes power to the appropriate subsystems. Additional power may be routed to portable multichannel analyzer 408, and to provide voltages and currents to x-ray detector 416.

Energy, or x-ray, source 410 receives power from battery 404 and control from readout, or control, box 412. Status of detection system 400 may be reported to system monitor 420 for formatting and routing to local computer 422. Data from x-ray detector 416 may be routed through portable multichannel analyzer 408, system monitor 420, and data interface 424 to local computer 422. Local computer 422 may be any device or component having a processor coupled to a memory, wherein the memory may store instructions to be executed on the processor. Alternatively, local computer 422 may be a processor itself.

Detector collimator 414 collects energy components to deliver to x-ray detector 416. X-ray detector 416 may be cooled by cooling mechanism 418. Cooling mechanism 418 may be stand-alone.

Beam 110 and beam 310 are disclosed above. These beams are transmitted from energy sources within the disclosed embodiments. Beams used by the disclosed embodiments may have the following characteristics. The x-ray source spot size may be about 0.25 mm×0.45 mm. The beam may expand by 35 degrees including angle. The disclosed embodiments may utilize several types of optics, including nested grazing incidence types and polycapillary arrays. One difficulty in trying to collimate x-rays may result from not deflecting well in high-index media. Reflection may work efficiently at grazing incidence angles less then about 1.5 degrees. Nested grazing incident surfaces may be fabricated and evaluated, but alignment and surface properties may be critical and time-consuming to implement. Polycapillary optics are preferred for their simplicity and ease of use and may be composed of many capillaries bent slightly to reflect the x-rays along the interior of the capillaries. Typical concentrations of energy on a target are of order 10 compared to an uncollimated beam. A collimated beam of 200 mm FWHM at about 2 meters standoff may be realized with the disclosed embodiments.

Referring back to FIG. 4, data from x-ray detector 416 may be captured by portable multichannel analyzer having about 8000 (max) channels at 12 µs/channel. Spectra from analyzer 408 may be sent to computer 422, or a similar device, to be computed to the database of elements and mixtures known to be contained in various substances. An immediate indication, such as a display with lights or screen, may be presented to an operator. Further, the data may be stored for archiving and future analysis within computer 422, or another location.

Referring to FIGS. 1 and 3, energy source 104 and energy source 304 may be placed in specific locations according to the disclosed embodiments. Energy source 104 may be mounted beside detector 122, as depicted in FIG. 1. The preferred angle between detector 122 and the field of view from the central axis of energy source 104 may be about 57 degrees. Energy source 304 may be mounted below detector 324, as depicted in FIG. 3. The preferred angle B between detector 324 and the field of view from the central axis of energy source 304 may be about 25 degrees to about 40 degrees. More preferably, angle B is about 34.5 degrees. Physical balance and ease of shielding may be considerations for the configuration depicted in FIG. 3.

Referring to FIGS. 3 and 4, components depicted in FIG. 3 comprise a detection module for the disclosed embodiments. The detection module may be connected to the support module, or backpack 330, with a single wire bundle 332. Multichannel analyzer 408, computer 422, controller 406, and battery 404 of FIG. 4 may be located remotely in the support module, and carried by the operator. The modular construction may allow quick replacement of any of the components in the field by non-experienced or untrained personnel. Self-calibration and internal subsystem function checking by computer 422 may assure accurate and complete operation in the field and after any component replacement.

Personnel should be shielded from the x-rays from energy source 304, or energy source 110, to a level below 0.5 R/hr within any location except directly in the source, or transmit, beam, such as source beam 310. A thin-sheet lead shielding may provide the shielding placed behind source 110 between the source tube area and the operator. In FIG. 3, personnel should not be in front of the equipment during operations because suspected explosive devices may be present. Source bleed through to x-ray detector 324 may be kept below the detection threshold with a thin lead sheet placed on the mount plate between energy source 304 and the entrance aperture of detector collimator 322. Without this shielding, various materials may be excited by source beam 310 in the vicinity of the aperture for detector collimator 322. Some of the excited photons may enter the active portion of the assembly of detector 324 and degrade the signal to noise performance of detection system 300. Further, scattered x-ray energy from soils, suitcases, air, and other substances in front of the instrument may be evaluated and mitigated on a case-specific basis with regard to personnel dose. The appropriate shielding or operational procedure then may be implemented.

In order to automate the disclosed embodiments for field operation, a step-scan platform may be utilized. The step-scan platform may be under the control of a computer, such as computer 422 in FIG. 4. An instrument is stepped to a new position horizontally, or in the "x" direction when an exposure is complete for an about 200 mm wide region in the area of interests. This process may be repeated until the disclosed embodiments scans a path horizontally, for example, + or − about 1 meter. The disclosed embodiments then may be stepped in the "y" direction by an amount slightly less than the active beamwidth and the "x" scan may be repeated. The process may be made rapid, and may continue until a substantial area, for example, about 4 square meters, are scanned. The operator then may physically move the instruments of the disclosed embodiments to the adjacent area for scanning. Because the instrument detection module of the disclosed embodiments weighs less than 15 kilograms, operations may allows personnel to perform a large area clearing on a continuous basis for long periods.

The disclosed embodiments may include customized proprietary software that determines the presence of explosives, distinguishes between explosive types, and translates the determinations into visual outputs that may be displayed on a computer screen, such as computer 422, or a display module, such as monitor and display 240. The software architecture may accommodate any controlled or desired substances.

According to the disclosed embodiments, a computer screen may display the proprietary preset adjustable parameters, such as multichannel analyzer channel ranges, the resultant spectra, and the results of the explosive determination. The explosive determination may identify if a certain class of explosive is present. Further, the explosive determination may identify the general type of explosive, such as RDX, TNT, C4, and the like. The computer, such as computer 250 or computer 422, also may act as the controller to the disclosed embodiments by providing the capability to customize all the various parameters for a given terrain, field conditions, luggage types, and the like. The disclosed embodiments also may be capable of providing "what-if" scenarios by retrieving and evaluating previous data under different selected test conditions or test parameters.

The disclosed embodiments may include analysis software written in Microsoft® Visual Basic. The analysis software may compare detector counts in one or more channel ranges to a selectable set of references ranges to determined measured count differences greater than a set of selectable differences. Previously obtained data for each substance may be used to determined the channels and ranges. Operating conditions, such as background values and scattered x-ray counts, may be used to determine the compared values for a "detect" or "no detect" condition.

A preferred embodiment may use a customized display module that presents the results of an explosive determination through the use of illuminated light-emitting diodes ("LEDs"). The display module may be designed to indicate "all clear" if no explosive or controlled substances are present, "explosive" if one of the pre-selected explosive types are identified, "re-shoot" if the software embodiments are uncertain in determining the presence of explosives or controlled substances, or "iron" if an unusually high iron content is present which indicates a potential metal casing for an explosive, such as a metal land mine. In addition, the display module may provide a visual display of the status of the disclosed embodiments by indicating "fault" if a monitored parameter is not functioning properly, "ready" if the system is ready to acquire another data point, or "acquiring" if the system is in the process of acquiring another set of data points.

Calculated detection sensitivity for the disclosed embodiments may be 10 parts per million ("ppm") with a spatial resolution of 0.1 meter using a 200 second integration time. The present invention is not limited to those portions of the electromagnetic spectrum covered by the disclosed embodiments. For example, higher energy detection systems may be capable of detecting elements that fluorescence at higher energies using the disclosed embodiments.

Figure 5:
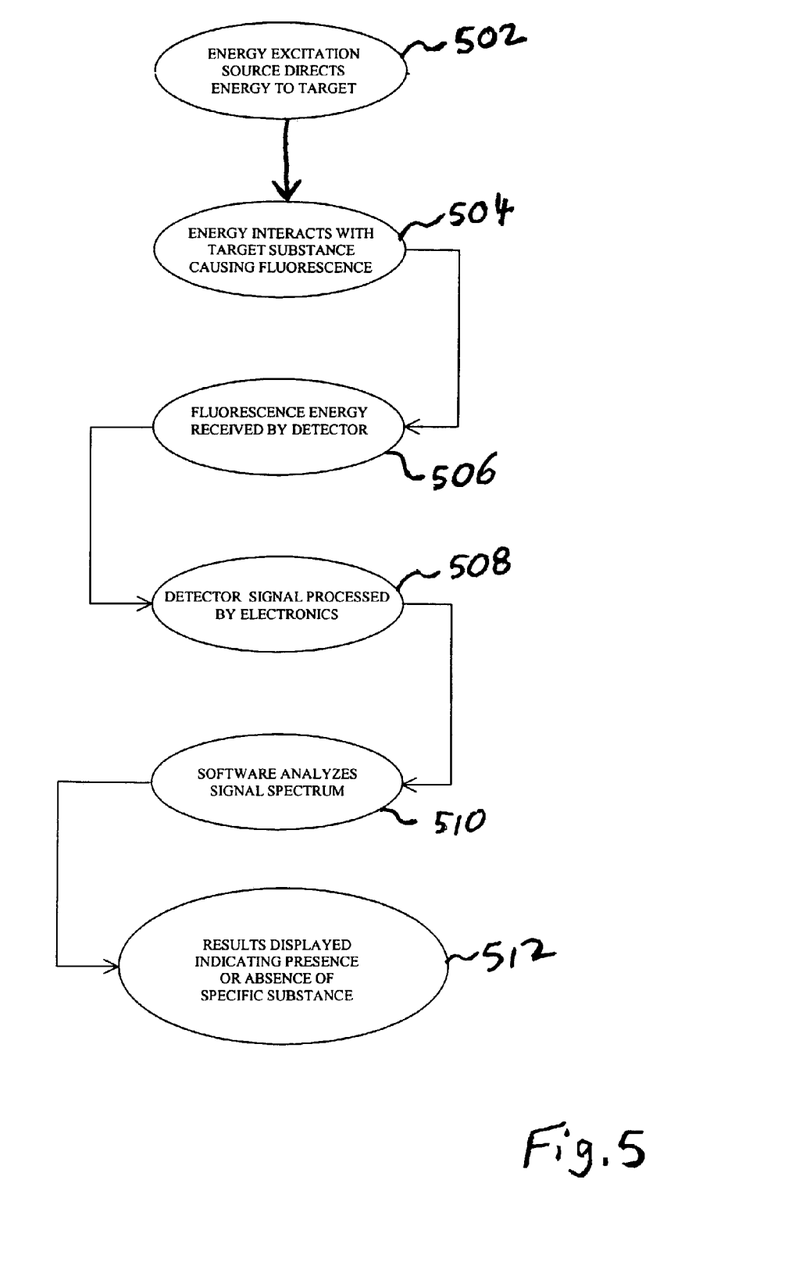
FIG. 5 illustrates a flowchart for detecting substances using x-ray fluorescence according to the disclosed embodiments.

FIG. 5 depicts a flowchart for detecting substances using x-ray fluorescence according to the disclosed embodiments. The flowchart may correspond with the processes and methods disclosed above. Step 502 executes by directing energy, such as x-rays, to a target from an energy excitation source. The target may be a container that does or does not contained controlled substances, explosives, and the like. Step 504 executes by interacting the energy with the target substance that causes fluorescence. Step 506 executes by receiving the fluorescent energy given off by the substance at a detector. Preferably, the fluorescent energy is x-ray energy.

Step 508 executes by processing the detector signal from the detector with electronics and algorithms. Step 510 executes by analyzing the signal spectrum with the software embodiments disclosed above. Step 512 executes by displaying results that indicate presence or absence of a specific substance.

The disclosed embodiments provide a detection system and method that achieves advantages over known systems and methods for detecting substances, such as controlled substances, explosives, and the like. Features of the disclosed embodiments may include a unique system physical configuration and critical component placement. Another feature may be using the unique energy signatures of landmines and explosive to detect and classify these items. Another feature of the disclosed embodiments may be the methods of energy tuning the energy, or x-ray, source. Another feature may be a software data analysis method and graphical user interface to communicate results from the detection processes disclosed herein. Another feature may be the application of x-ray fluorescence to controlled or dangerous substances, or explosives. Another feature may be the annealing process of the x-ray detector, as disclosed above.

Thus, according to the disclosed embodiments, an operator may aim the energy source at a container, luggage, an area on a surface, and the like. A beam of x-rays may illuminate the area or item. The beam energy interacts with the substance, thereby giving off fluorescent energy. The operator does not need to open the container or surface to complete analysis testing. The time or effort to open or access the substance is reduced. Further, costs in terms of damaged items or injury to personnel is reduced.

The disclosed embodiments may include an x-ray fluorescent detector that includes a platform with an x-ray generator and a detector within a specific range of angles relative to each other. The x-ray generator may have a collimator and x-ray optics to define an energy, or x-ray, beam directed at a target. The target may be a controlled, dangerous, or explosive substance. The substance is irradiated to induce fluorescent x-ray energy. An x-ray detector produces an output signal in response to the induced fluorescent x-ray energy from constituents in the target substance. The disclosed embodiment also may include a controller that adjusts the beam voltage and current in the x-ray generator. The controller causes the output signal to be presented to a multichannel analyzer for a period of time known as an integration time.

It will be apparent to those skilled in the art that various modifications and variations can be made in the wheel assembly of the present invention without departing from the spirit or scope of the invention. Thus, it is intended that the present invention cover the modifications and variations of this invention provided that they come within the scope of any claims and their equivalents.

What is claimed is:

1. A system for detecting a substance, comprising:
    an energy source to transmit an x-ray beam at a target to produce fluorescent energy;
    an x-ray detector to detect said fluorescent energy from said target, wherein said x-ray detector is at an angle to said energy source;
    an active cooling mechanism to cool said x-ray detector;
    a multichannel analyzer to receive said fluorescent energy from said x-ray detector; and
    a computer coupled to said multichannel analyzer to determine whether said fluorescent energy corresponds to said substance,
    wherein the system is operable at large standoff distances of at least about one meter.

2. The system of claim 1, further comprising a controller coupled to said energy source, wherein said controller provides power and control to said energy source.

3. The system of claim 1, further comprising a display to indicate status to a user of said detection system, wherein said display is coupled to said computer.

4. The system of claim 1, further comprising a shielded enclosure around said energy source.

5. The system of claim 1, wherein said angle is about 45 degrees to about 65 degrees.

6. The system of claim 1, wherein said substance is an explosive.

7. The system of claim 1, wherein said substance is a controlled substance having certain chemical properties.

8. The system of claim 1, wherein said energy source is a tungsten output source.

9. The system of claim 1, wherein said x-ray detector is annealed.

10. A portable system for detecting a substance under a surface, wherein said system includes a detection module and a support module, comprising:
    an energy source within said detection module to transmit an x-ray beam at a surface location, wherein said energy source is mounted on an equipment support;
    an x-ray detector within said detection module to detect fluorescent energy from a vapor plume corresponding to said surface location, wherein said x-ray detector is at an angle relative to said energy source and mounted on said equipment support;
    an active cooling mechanism to cool said x-ray detector;
    a portable multichannel analyzer within said support module to receive said fluorescent energy;
    a computer within said support module coupled to said portable multichannel analyzer to determine whether said fluorescent energy corresponds to said substance; and
    a battery within said support module to supply power to said detection module and said support module,
    wherein the system is operable at large standoff distances of at least about one meter.

11. The portable system of claim 10, wherein said support module is a backpack.

12. The portable system of claim 10, further comprising a readout box coupled to said support module to display information.

13. The portable system of claim 10, wherein said substance under said surface is an explosive.

14. The portable system of claim 10, wherein said angle is about 25 degrees to about 40 degrees.

15. A method for detecting a substance, comprising:
    directing an x-ray beam at a target from an energy source, the target located at a large standoff distance of at least about one meter;
    interacting said target with said beam to produce fluorescent energy;
    detecting said fluorescent energy from an x-ray at an angle from said energy source using an actively cooled x-ray detector;
    analyzing said fluorescent energy to determine whether said fluorescent energy corresponds to said substance.

16. The method of claim 15, wherein said analyzing includes comparing said fluorescent energy to a signal spectrum of known substances.

17. The method of claim 15, further comprising indicating whether said target is said substance.

18. The method of claim 15, further comprising processing said fluorescent energy with a multichannel analyzer.

19. A method for detecting a substance, comprising:
    providing power to an energy source to transmit an x-ray beam to large standoff distances of at least about one meter;
    producing fluorescent energy from an item in response to said x-ray beam;
    detecting said fluorescent energy over an integration period at an actively cooled x-ray detector;
    processing said fluorescent energy; and
    determining whether said item is said substance according to said fluorescent energy.

20. The method of claim 19, further comprising moving said item on a conveyor belt.

21. The method of claim 19, further comprising adjusting said x-ray beam using a controller coupled to said energy source, to compensate for background noise.

* * * * *